(12) United States Patent
Kuchař et al.

(10) Patent No.: US 6,303,612 B1
(45) Date of Patent: Oct. 16, 2001

(54) DERIVATIVES OF HYDROXYPHENYLSULFANYLBENZOIC AND HYDROXPHENYLSULFANYLARYLACETIC ACIDS

(75) Inventors: Miroslav Kuchař; Vojtěch Kmoníček; Vladimíra Panajotová; Bohumila Brůnová; Antonín Jandera; Hana Jiříčková; Věra Bucharová, all of Praha (CZ)

(73) Assignee: Leciva, A.S., Praha (CZ)

( * ) Notice: Subject to any disclaimer, the term of this patent is extended or adjusted under 35 U.S.C. 154(b) by 0 days.

(21) Appl. No.: 09/736,020
(22) PCT Filed: Jun. 16, 1999
(86) PCT No.: PCT/CZ99/00019
  § 371 Date: Dec. 19, 2000
  § 102(e) Date: Dec. 19, 2000
(87) PCT Pub. No.: WO99/67208
  PCT Pub. Date: Dec. 29, 1999

(30) Foreign Application Priority Data

Jun. 19, 1998 (CZ) ...................................................... 1941-98

(51) Int. Cl.[7] ...................... A61K 31/495; C07D 241/04
(52) U.S. Cl. ........................... 514/255; 544/398; 544/399; 546/152; 546/174; 562/431; 562/432; 514/311; 514/557
(58) Field of Search .................................... 514/557, 255, 514/311; 562/431, 432; 546/174, 152; 544/398, 399

(56) References Cited

U.S. PATENT DOCUMENTS 5,109,009  4/1992  Nielsen et al. .
5,462,954  10/1995  Baker et al. .

FOREIGN PATENT DOCUMENTS 0 544 488  6/1993  (EP) .

OTHER PUBLICATIONS

Chemical Abstracts, AN 1986:626368, JP 61 130271, Jun. 18, 1986.
E. Gonsior, et al., Database Chemabs Online! Abstracts Service, AN 1979:568618, "Protective Antiallergic Effects of a New Coumarin Compound (BM15,100) in Experimental Asthma," 1979.

*Primary Examiner*—Charanjit S. Aulakh
(74) *Attorney, Agent, or Firm*—Oblon, Spivak, McClelland, Maier & Neustadt, P.C.

(57) ABSTRACT

Processes for the preparation of derivatives of hydroxyphenylsulfanylbenzoic and hydroxyphenylsulfanylarylacetic acids of Formula (I) and pharmaceutical compositions including these compounds are provided:

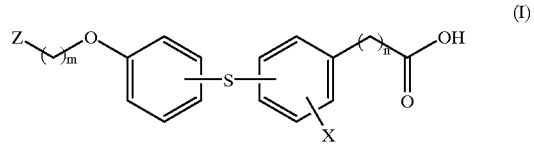

(I)

wherein X is H, halogen or $NO_2$ group, n is 0 or 1, and m is 2 to 4 if Z is either 4-acetyl-3-hydroxy-2-propylphenoxy of Formula (II):

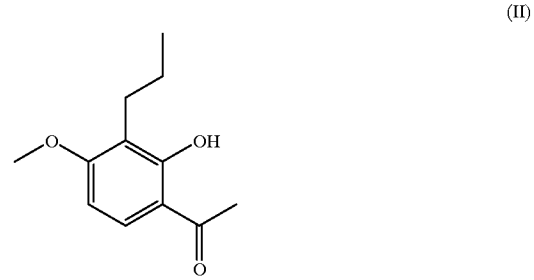

(II)

or a piperazinyl residue, or m is 1 if Z is quinolin-2-yl or 6-chloroquinoli-2-yl.

6 Claims, No Drawings

DERIVATIVES OF HYDROXYPHENYLSULFANYLBENZOIC AND HYDROXPHENYLSULFANYLARYLACETIC ACIDS

TECHNICAL FIELD

The invention concerns derivatives of hydroxyphenylsulfanylbenzoic and hydroxyphenylsulfanylarylacetic acids, methods of their synthesis and pharmaceutical preparations with antiinflammatory and/or antiasthmatic activities produced of them.

BACKGROUND ART

The products of arachidonic acid biotransformation play an important role in pathological processes of inflammation. Leukotrienes, as pathophysiological mediators of asthma and various inflammatory diseases, originate with the oxidative metabolism of arachidonic acid in the presence of lipoxygenases (Taylor G. W., Clarke S. R.: *Trends Pharmacol. Sci.* 7, 100 (1986)). Compounds influencing the biosynthesis of leukotrienes and antagonizing their biological functions are in the focus of research interest. Peptide leukotrienes $C_4$, $D_4$ and $E_4$ are characterized as components of, slow reacting substance A" (SRS-A), which induces anaphylactic reaction (Samuelson B.: *Science* 22, 563 (1983)). The SRS-A is a mediator of inflammation in bronchial constriction and increases the vascular permeability in diseases associated with acute hypersensitivity (von Sprecher A. et al.: *Chimia* 46, 304 (1992)). Furthermore, it has been observed that it stimulates aggregation and degranulation of human neutrofils and promotes chemotaxis and chemokinesis of leukocytes and other cells which are involved in the development of the inflammatory process (Djuric S. W. et al.: *Drugs Fut.* 17, 819 (1992)). Another leukotriene, $LTB_4$, is a mediator in the release of lysosomal enzymes and stimulates the formation of superoxide. Therefore, this substance is supposed to be an important mediator in many inflammatory diseases (Bray M. A.: *Agents Actions* 19, 1 (1986)). In connection with this pathological performance of leukotrienes, great attention has been devoted to the utilization of antileukotrienics for the treatment of allergic respiratory diseases. The compounds characterized by combined antileukotrienic effects appear to be especially advantageous. Now it has been found that the title acids connected with suitable structural fragments offer substances with multiple mechanism of antileukotrienic activity, for instance with inhibition of LT biosynthesis combined with antagonistic effect towards peptidoleukotrienes. Fragments used for this purpose, e.g. the 2,4-dihydroxyacetophenone or 2-hydroxymethylquinoline radicals, are known pharmacophores of selective $LTD_4$ antagonists (Dillard R. D. et al.: *J. Med. Chem.* 34, 2768 (1991), Sirois B. et al.: *Agents Actions* 34, 117 (1991)).

DISCLOSURE OF THE INVENTION

The invention consists in new derivatives of hydroxyphenylsulfanylbenzoic and hydroxyphenylsulphanylarylacetic acids of the general formula I

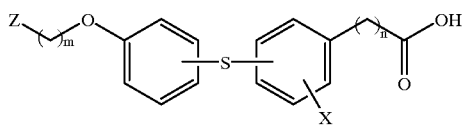

in which X represents H, a halogen or $NO_2$ group, n represents 0 or 1 m represents 2 to 4, if Z is 4-acetyl-3-hydroxy-2-propylphenoxy II (II)

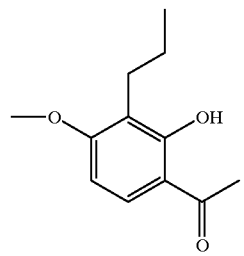

or a piperazine residue of the general III, in which R represents an alkyl $C_1$–$C_4$, benzyl, substituted benzyl or carboxymethoxyethyl, (III)

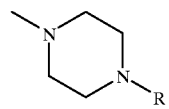

or m represents 1, if Z is 2-quinolinyl of the general formula IV, in which R' represents H or a halogen (IV)

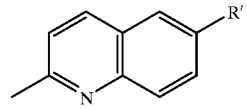

Compounds of the general formula I can be prepared by organic synthetic methods, the compounds bearing the residue Z=II or III being advantageously prepared by reacting an ester of ω-haloalkoxy phenylsulfanylbenzoic or -arylacetic acid of the general formula V

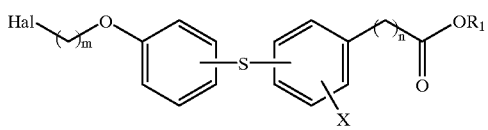

in which Hal represents a chlorine, bromine or iodine atom, $R_1$ represents a lower alkyl, preferably methyl or ethyl, m, n and X represent the same as in formula I, with a compound of the general formula VI

Z—H (VI)

in which Z has the same meaning as in formulas II and III. The reaction of compounds V and VI may be carried out usually in the presence of a suitable organic or inorganic base, preferably in the presence of an anhydrous alkali metal carbonate or an alkali metal hydroxide or triethylamine or trimethylamine, in a boiling lower ketone, typically in acetone or 2-butanone. The esters obtained may be converted to the corresponding acids I by the use of usual methods of hydrolysis, for instance by influence of an alkaline hydroxide in an aqueous-alcoholic solution at the temperature of 60–110° C., preferably at the boiling temperature of the employed aqueous-alcoholic mixture. The resulting alkali salt may be transferred into the free acid by the use of an acceptable organic or inorganic acid.

Compounds I bearing the fragment Z of the general formula II or IV may be likewise prepared by reacting hydroxyphenylsulfanylbenzoate or hydroxyphenylsulfanylarylacetate of the general formula VII

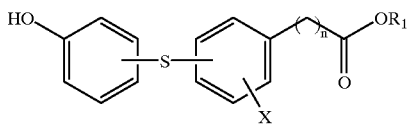

in which n and X haze the same meaning as in formula I and $R_1$ represents the same as in formula V with a compound of general formula VIII

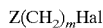   (VIII)

in which Z is as defined in formulae II and IV, m has the same meaning as in formula I and Hal represents chlorine, bromine or iodine.

Compounds I, including their pharmaceutically harmless salts with inorganic or organic bases, which are the object of the invention, are characterized by significant inhibitory activity for leukotrienes (LT) biosynthesis and also by having a high affinity to LT receptors. Both effects are important for the antiinflammatory and antiasthmatic activity of these substances in pharmaceutical preparations which are a further object of the invention. They are at the same time characterized by low toxicity including absence of ulcerogenic effect. These compounds may be used for the preparation of therapeutic compositions containing the active substance in a mixture with pharmaceutically suitable adjuvants, liquid or solid, usually used in the production of drug formulations. Biological activities of compounds I were determined in the following tests:

Ex vivo Inhibition of $LTB_4$ Production

The production of $LTB_4$ was determined in rat polymorphonuclear cells from pleural exudate elicited by heat-activated rat serum (Palmer R. M. J., Salmon J. A.: *Immunology* 50, 65 (1983)). The cells were stimulated with the Ca ionophore A 23187 (Sigma) and incubated with various concentrations of the drugs tested. The sample containing only buffer was used for the determination of unaffected biosynthesis; the complete inhibition was measured in a sample with 100 μg of NDGA in 1 ml. $LTB_4$ was determined in supernatant using a commercial RIA kit (Amersham).

$LTB_4$ Receptor Binding Study

A slightly modified method of Cheng and coworkers (Cheng J. B. et al.: *J. Pharm. Expl. Ther.* 236, 126 (1986)) was used. The membrane fraction was prepared from male guinea-pig spleen; 2 mg of membranes were incubated with 0.3 nM $^3H$-$LTB_4$ at 25° C. for 30 min in 100 μl of the incubated mixture. The nonspecific binding was determined in the presence of 0.1 μM $LTB_4$. The membranes were filtered though Whatman GF/C paper and washed triply with buffer. The radioactivity was measured by liquid scintillation spectrometry, and the specific binding of $^3H$-$LTB_4$ to the receptor was determined.

$LTD_4$ Receptor Binding Study

This study was performed according to the method of Burns and coworkers (Burns R. F. et al.: *Life Sci.* 33, 645 (1983)). The membrane fraction was prepared from male guinea-pig lungs, and 4 mg of this fraction were incubated with 0.4 nM $^3H$-$LTD_4$ for 60 min at 25° C. in 100 μl of the incubated mixture. The nonspecific binding was determined in the presence of 0.1 μM $LTD_4$. The filtration of the membranes, washing, and radioactivity measurement were as above.

Antioxidant Effect in vitro

A modified method (Ohkawa H.: *Anal Biochem.* 95, 351 (1979)) utilizing the peroxidation of lipids from the hepatic cells membranes was used for the determination of antioxidant effect. The end-product, malonic dialdehyde, was transformed to coloured complex with thiobarbituric acid and determined spectrophotometrically. The antioxidant effect was expressed in % of peroxidation inhibition in the presence of the compound tested in comparison to a control sample.

Inhibition of Carrageenan Edema (Winter J.: *Proc. Soc. Expl. Biol. Med* 111, 544 (1962) The edema of hind pad was induced by intrapleural injection of 0.5% carrageenan in physiological solution to Wistar-Han rats. The volume of edema was measured by volumometer (Ugo Basile) 1.5, 3, 4.5 and 6 h following the carrageenan injection. The effect was expressed by the inhibition of edema in comparison with an untreated group of animals.

Inhibition of Carrageenan-induced Pleuritis in Rats (Hidaka T. J.: *Pharm. Pharmacol.* 38, 242 (1986) 1 ml of 0.5% carrageenan solution in saline was administered intrapleurally to experimental animals under mild ether anesthesia. Test drugs were administered in single oral dose 1 h before carrageenan injection, 4 h following the carrageenan application the rats were killed and exudate was withdrawn from opened pleural cavity. The volume of exudate, its cellularity and total cell number were determined.

Inhibition of Arachidonic Acid-induced Ear Inflammation in Mice (Opas E. E. et al.: *J. Invest. Dermatol.* 84, 253 (1985) Ear inflammation was induced in male mice by 20 μl of arachidonic acid dissolved in acetone (concentration 100 mg/ml). The mice were sacrificed 1 h after application of arachidonic acid and the ears were cut off by standard means. The other, vehicle-treated ear of the same animal served as a control. The degree of ear hyperemia and the weight of ear lobes were evaluated. Test compounds were administered orally 1 h before the induction of inflammation.

Inhibition of Allergic Bronchospasm Induced by $LTB_4$ (Compound 48/80 or Ovalbumin, Respectively)

The modified method of Kreutner W. et al (Krelutner W. et al.: *Agents Actions* 28, 253 (1989)) was used. Bronchoconstrictioin was induced by intravenous injection of 1 μg/kg $LTD_4$ (3 mg/kg of compound 48/40 or 0.35 mg/kg of ovalbumin, respectively). In the case of oval-bumin, the animals were senzitized by intraperitoneal injection of ovalbumin (100 mg/kg) 14 days before induction. The compounds tested were applied 5 min before the administration of the inductor; the vehiculum used for the application of compound tested was administered to the control group of animals. The tracheal pressure was determined in the intervals of 2, 4 and 10 minutes after induction. The effect was expressed in percentage inhibition of bronchospasm relative to the untreated control.

The results of evaluation of biological activities are summarized in Tables I–IV. The most of compounds of invention are characterized by multiple antileukotrienic effect manifested itself by significant antiinflammatory and antiasthmatic activity.

The invention will now be described, by way of illustration, in the following Examples.

EXAMPLES

Example 1

Methyl 4-(4-Hydroxyphenylsulfanyl)benzoate

The stirred mixture of 60.0 g (0.23 mol) of 4-(4-methoxyphenylsulfanyl)benzoic acid and 180.0 g of pyridine. HCl was heated to 220–230° C. under nitrogen for 45 min. The mixture was cooled down to 90° C. and poured slowly under stirring into the ice water (1000 ml); the solid was filtered off, washed with water and dried at 75° C. 4-(4-Hydroxyphenylsulfanyl) benzoic acid was obtained in a yield of 56.0 g (98.2%); m.p. 196–200° C. A solution of 46.9 g (0.19 mol) of the above acid in 480 ml of methanol was filtered with charcoal, 5 ml of concentrated $H_2SO_4$ was added and the mixture was heated to boil for 18 h. One half of methanol was evaporated and the rest was poured into the ice water (600 ml) the solid was filtered off and was washed by water. Methyl 4-(4-hydroxyphenylsulfanyl)benzoate was obtained in a yield of 39.0 g (78.9%), m.p. 184–186° C. For $C_{14}H_{12}O_3S$ (260.3) calculated: 64.59% C, 4.65% H, 12.32% S; found: 64.52% C, 4.72% H, 11.99% S. Methyl esters in Examples 2–5 were prepared similarly to Example 1.

Example 2

Methyl 4-(3-Hydroxyphenylsulfanyl)benzoate 4-(3-Methoxyphenylsulfanyl)benzoic acid was washed up with pyridine.HCl and corresponding 4-(3-hydroxyphenylsulfanyl)benzoic acid was obtained in a yield of 90.9%, m.p. 172–174° C. The title ester was prepared by the reaction with methanol in the presence of $H_2SO_4$ concentrated in a yield of 82.9%, m.p. 86–87° C. (benzene/n-hexane). For $C_{14}H_{14}O_3S \cdot 1/2\ C_6H_6$ (299.3) calculated: 68.22% C, 5.05% H, 10.69% S; found: 68.49% C, 4.96% H, 10.94% S.

Example 3

Methyl 2-(3-Hydroxyphenylsulfanyl)benzoate 2-(3-Methoxyphenylsulfanyl)benzoic acid was worked up with pyridine.HCl and 2-(3-hydroxyphenylsulfanyl) benzoic acid was obtained in a yield 91.6%, m.p. 207–209° C. Thionyl chloride (24.4 g, 0.205 mol) was added to stirred methanol (250 ml) at −15° C. and this mixture was treated by a solution of the previous acid (33.5 g, 0.136 mol) in 200 ml of methanol. A mixture was stirred with cooling for 30 min and on the next day heated to boil for 6 h. After evaporation to 100 ml, the rest was poured under stirring into 300 g of ice. The solution was washed twice with ether (150 ml) and the organic layer was washed with saturated sodium hydrocarbonate, dried with sodium sulphate and solvent was removed by evaporation. The oil obtained was mixed up with n-hexane and gave crystals of pure methyl 2-(3-hydroxyphenylsulfanyl)benzoate in a yield of 27.9 g (78.8%), m.p. 77–78.5° C. For $C_{14}H_{12}O_3S$ (260.3) calculated: 64.59% C, 4.65% H, 12.32% S; found: 64.73% C, 4.75% H, 11.98% S.

Example 4

Methyl 2-(4-Hydroxyphenylsulfanyl)benzoate 2-(4-Hydroxyphenylsulfanyl)benzoic acid was worked up with pyridine.HCl and 2-(4-hydroxyphenylsulfanyl)benzoic acid was obtained in a yield of 96%, m.p. 193–196° C. This acid was subjected to esterification with a mixture of methanol and thionyl chloride (cf. example 3) and the expected methyl ester was obtained in a yield of 77.1%, m.p. 140–142° C. (chloroform). For $C_{14}H_{12}O_3S$ (260.3) calculated: 64.59% C, 4.65% H, 12.32% S; found: 64.53% C, 4.81% H, 11.96% S.

Example 5

Methyl 2-(4-hydroxyphenylsulfanyl)-5-nitrobenzoate 2-(4-Methoxyphenylsulfanyl)-5-nitrobenzoic acid was worked up with pyridine.HCL and corresponding 4-hydroxyacid was obtained in a yield of 97.5%, m.p. 204–207° C. This acid was subjected to esterification with a mixture of methanol and thionyl chloride (cf. example 3) and the crude ester obtained was purified by chromatography on silica gel. The expected methyl ester was obtained in a yield of 42.7%, m.p. 162–163° C. For $C_{14}H_{11}NO_5S$ (305.3) calculated: 55.07% C, 3.63% H, 4.59% N, 10.5% S; found: 54.54% C, 3.62% H, 4.61 N, 10.47% S.

Example 6

Methyl 4-(3-Hydroxyphenylsulfanyl)-3-nitrobenzoate 4-(3-methoxyphenylsulfanyl)-3-nitrobenzoic acid was worked up with pyridine.HCL and corresponding 3-hydroxy-acid was obtained in a yield 61.5%, m.p. 202–206° C. The expected methylester was obtained by the same manner as in example 3 in a yield 72.4%, m.p. 122–125° C.; $^1$H NMR $(CD_3)_2SO$, 60° C.: $CH_3$ 3.88 s, H(O) 9.82 bs, aromat. H(2) 8.63 d, J=1.6 Hz, H(6) 8.03 dd, J=1.6, 8.7 Hz; the rest of aromatic H 6.90–7.48 m.

Example 7

4-(4-(2-(4-Acetyl-3-hydroxy-2-propylphenoxy) ethyloxy)phenylsulfanyl)benzoic Acid (1)

A mixture of 7.7 g (0.03 mol) of 4-(2-chloroethoxy)-2-hydroxy-3-propylacetophenone, 7.8 g (0.03 mol) of methyl 4-(4-hydroxyphenylsulfanyl)benzoate, 13.8 g (0.1 mol) of anhydrous potassium carbonate and 0.6 g of sodium iodide in 160 ml of 4-methyl-2-pentanone was heated to boil for 45 h. The precipitate was filtered off, the filtrate evaporated to dryness and the solid rest was dissolved in 20 ml of dichloromethane and purified on silica gel using dichloromethane as eluent. The methylester of the title acid was isolated by evaporation of a medium fraction in a yield of 8.4 g (58.2%), m.p. 117–119° C.; for $C_{27}H_{28}O_6S$ (480.6) calculated: 67.48% C, 5.87% H, 6.67% S; found: 67.31% C, 5.89% H, 6.67% S. A stirred mixture of 8.0 g (0.017 mol) of the previous methylester dissolved in 40 ml of ethanol and a solution of 3.3 g of potassium hydroxide in 10 ml of water was heated to boil for 30 min. Ethanol was evaporated and the rest was diluted by 20 ml of water and the troubled solution was filtered with charcoal. The clear filtrate was cooled by ice water and acidified to pH 1 with dilute hydrochloric acid. The precipitated solid was extracted into chloroform (3×40 ml), the extracts were washed with water, dried by sodium sulphate and the solvent was evaporated. The crude product (7.7 g, m.p. 134–137° C.) was crystallized from methanol. The purified title acid was obtained in a yield of 5.5 g (69.9%), m.p. 146–148° C. For $C_{26}H_{26}O_6S$ (466.6) calculated:66.93% C, 5.61% H, 6.87% S; found: 66.74% C, 5.61% H, 6.99% S. $^1H$ NMR ($C^2HCl_3$): $CH_3$(CO) 2.58 s: H(O) 12.75 s; aromatic H-atoms on the nucleus bearing carboxyl: H (2, 6) 7.93 d (J=8.9 Hz), H (3, 5) 7.01 d (J=8.9 Hz).

The acids in examples 8–11 were prepared similarly to example 7:

Example 8

4-(3-(2-(4-Acetyl-3-hydroxy-2-propylphenoxy) ethyloxy)phenylsulfanyl)benzoic Acid (2)

The reaction of methyl 4-(3-hydroxyphenylsulfanyl) benzoate with 4-(2-chloroethoxy)-2-hydroxy-3-propylacetophenone was carried out in a yield of 26.1%. The title acid was prepared by subsequent hydrolysis in 67.0% yield, m.p. 144–146° C. (70% ethanol). For $C_{26}H_{26}O_6S$ (466.6) calculated:66.93% C, 5.61% H, 6.87% S; found: 66.88% C, 5.83 %, 6.68% S; $^1H$ NMR ($C^2H_3)_2SO$, 60° C.): $CH_3(CO)$ 2.57 s; H (O) 12.77 s; aromatic H-atoms on the nucleus bearing carboxyl: H (2,6) 7.83 m, H (3,5) 7.33 m.

Example 9

2-(3-(3-(4-Acetyl-3-hydroxy-2-propylphenoxy) propoxy)phenylsulfanyl)benzoic Acid (6)

Methyl ester of title acid was prepared from methyl 2-(3-hydroxyphenylsulfanyl)benzoate and 4-(3-chloropropoxy)-2-hydroxy-3-propylacetophenone in a yield 59.0%, m.p. 73–75° C. (methanol). The title acid was prepared by subsequent hydrolysis in a yield 78.2%, m.p. 142–144° C. (ethanol). For $C_{27}H_{28}O_6S$ (480.6) calculated: 67.48% C, 5.87% H, 6.67% S; found: 67.26% C, 5.94% H, 6.51% S; $^1H$ NMR (CDCl$_3$): $CH_3(CO)$ 2.56 s; H (O) 12.73 s; aromatic H-atoms on the nucleus bearing carboxyl: H(6) 8.13 bd; H (3,4,5) 6.78–7.46 m.

Example 10

4-(3-(4-(4-Acetyl-3-hydroxy-2-propylphenoxy) butoxy)phenylsulfanyl)-3-nitrobenzoic Acid (9)

Crude methyl ester of the title acid was prepared from methyl 4-(3-hydroxyphenylsulfanyl) -3-nitrobenzoate and 4-(4-bromobutoxy)-2-hydroxy-3-propylacetophenone in 100% yield (viscous oil), which was hydrolyzed to corresponding acid in a yield of 40.5%; m.p. 116–118° C. (60% acetone). For $C_{28}H_{29}NO_8S$ (539.6) calculated: 62.32% C, 5.42% H, 2.59% N, 5.94% S.; found: 62.15% C, 5.62% H, 2.39% N, 5.95% S; $^1H$ NMR ($C^2H_3)_2SO$, 60° C.): $CH_3(CO)$ 2.56 s. H (O) 12.76 s, aromatic H-atoms on the nucleus bearing carboxyl: H (2) 8.64 d (J=2.1 Hz), H (5)7.05 d (J=8.7 Hz), H (6) 8.1 dd (J=2.1, 8.7 Hz).

Example 11

2-(4-(4-(4-Acetyl-3-hydroxy-2-propylphenoxy) butoxy)phenylsulfanyl)-5-nitrobenzoic Acid (10)

Methylester of the title acid was prepared from methyl 2-(4-hydroxyphenylsulfanyl)-5-nitro-benzoate and 4-(4-bromobutoxy)-2-hydroxy-3-propylacetophenone in a yield of 42.8%, m.p. 169–171° C. (acetone). For $C_{28}H_{29}NO_8S$ (539.6) calculated: 62.32% C, 5.42% H, 2.59% N, 5.94% S.; found: 62.23% C, 5.65% H, 2.41% N, 6.05% S; $^1H$ NMR ($C^2H_3)_2SO$, 60° C.): $CH_3(CO)$ 2.57 s, H (O) 12.78 s, aromatic H-atoms on the nucleus bearing carboxyl: H (3) 7.78 d (J=9.0 Hz), H (4) 8.12 dd (J=2.5, 9.0 Hz), H (6) 8.64 d (J=2.5 Hz).

Example 12

Methyl 4-(3-(3-Chloropropoxy)phenylsulfanyl) benzoate

The mixture of 11.7 (44.5 mM) of methyl 4-(3-hydroxyphenylsulfanyl)benzoate, 23.6 g (0.15 mol) of 3-bromnochloropropane and 14.0 g potassium carbonate in 200 ml of 4-methylpentane-2-one was heated to boil for 10 h. After cooling to 20° C., the precipitate was filtered off and the filtrate was evaporated to an oil. The rest was dissolved in 20 ml of ether, diluted with 20 ml of n-hexane and after standing in a refrigerator, the crystalline product was filtered off in a yield of 78.0%, m.p. 47–49° C. For $C_{17}H_{17}ClO_3S$ (336.8) calculated: 60.62% C, 5.09% H, 10.52% Cl, 6.52% S; found: 60.65% C, 5.12% H, 9.25% Cl, 9.25% S.

Methyl esters in examples 13 and 14 were prepared similarly to example 12.

Example 13

Methyl 2-(3-(3-Chloropropoxy)phenylsulfanyl) benzoate

It was prepared from methyl 2-(3-hydroxyphenylsulfanyl)-benzoate and 1-bromo-3-chloropropane as an oil in a yield of 85.0%. For $C_{17}H_{17}ClO_3S$ (336.8) calculated: 60.62% C, 5.09% H, 10.52% Cl, 9.52% S; found: 60.46% C, 5.09% H, 10.35% Cl, 9.42% S.

Example 14

Methyl 4-(4-(3-Chloropropoxy)phenylsulfanyl) benzoate

The title compound, having m.p. 65–67° C., was obtained in 92.8% yield from methyl 4-(4-hydroxyphenylsulfanyl) benzoate and 1-bromo-3-chloropropane. For $C_{17}H_{17}ClO_3S$ (336.8) calculated: 60.62% C, 5.09% H, 10.52% Cl, 9.52% S; found: 60.52% C, 5.14% H, 10.49% Cl, 9.15% S.

Example 15

Methyl 4-(3-(4-Bromobutoxy)phenylsulfanyl) benzoate

A stirred mixture of methyl 4-(3-hydroxyphenylsulfanyl) benzoate (13.0 g, 50.0 mmol) and 1,4-dibromobutane (21.0 g, 0.1 mol), anhydrous potassium carbonate (16.0 g) and 4-methylpentane-2-one (150 ml) was refluxed for 13 h. The hot mixture was filtered, the filtrate was evaporated to dryness and the partially crystalline residue was dissolved in a mixture of dichloromethane-petroleum ether (1:1) and then purified by column chromatography on silica gel using the same solvent mixture. The title ester was obtained as the main fraction (15.2 g, 76.9%), m.p. 43–45° C. For $C_{16}H_{19}BrO_3S$ (395.3) calculated: 54.69% C, 4.84% H, 20.22% Br, 8.11% S; found: 54.71% C, 4.80% H, 20.09% Br, 8.07% S.

Example 16

4-(4-(3-(4-Acetyl4-3-hydroxy-2-propylphenoxy) propoxy)phenylsulfanyl)benzoic Acid (3)

A mixture of methyl 4-(4-(3-chloropropoxy) phenylsulfanyl)benzoate (9.0 g, 26.5 mmol), 2,4-dihydroxy- 3-propylacetophenone (5.2 g, 26.5 mmol), anhydrous potassium carbonate (18.0 g), potassium iodide (0.8 g) and 4-methylpentane-2-one (160 ml) was refluxed for 24 h under nitrogen atmosphere. The hot mixture was filtered, the filtrate was decolorized with refrigerator and the formed insoluble portion was filtered, washed with ether and crystallized from methanol to give methyl ester of the title acid (50.4%), m.p. 58–61° C. For $C_{28}H_{30}O_6S$ (494.6) calculated: 68.00% C, 6.11% H, 6.48% S; found: 67.65% C, 6.14% H, 6.38%. A solution of potassium hydroxide (2.25 g, 40.0 mmol) in water (10 ml) was added to a stirred solution of this ester (6.2 g, 12.5 mmol) in ethanol (30 ml) and the mixture was refluxed for 30 min. The solution after evaporation of ethanol was neutralized with acetic acid, the mixture was cooled down and the formed insoluble portion was filtered and washed with water. The crude product was crystallized from methanol (150 ml) to give the title acid (58.4%), m.p. 177–179° C. For $C_{27}H_{28}O_6S$ (480.6) calculated: 67.48% C, 5.87% H, 6.67% S; found: 67.35% C, 5.85% H, 6.40% S. $^1H$ NMR spectrum ($CDCl_3$): $CH_3(CO)$ 2.55 s; H(O) 12.72 s: aromatic H on the benzoic acid nucleus: H(2,6) 7.83 d (J=8.4 Hz); H(3,5) 7.04 d (J=8.4 Hz).

Using the procedure described in Example 16, acids described in Examples 17 and 18 were prepared.

Example 17

4-(3-(3-(4-Acetyl-3-hydroxy-2-propylphenoxy) propoxy)phenylsulfanyl)benzoic Acid (5)

The crude methyl ester of the title acid was obtained from methyl 4-(3-(3-chloropropoxy)-phenylsulfanyl)benzoate and 2,4-dihydroxy-3-propylacetophenone. Column chromatography on silica gel, using dichloromethane and chloroform as eluents, provided pure product (71.8%), m.p. 99–101° C. For $C_{28}H_{30}O_6S$ (494.6) calculated: 68.00% C, 6.11% H, 6.48% S; found: 67.68% C, 6.16% H, 6.49% S. After hydrolysis with a solution of potassium hydroxide and following acidic treatment with hydrochloric acid, the crude product was crystallized from aqueous methanol to give the title acid (94.6%), m.p. 104–106° C. For $C_{27}H_{28}O_6S$ (480.6) calculated: 67.48% C, 5.87% H, 6.67% S; found: 67.42% C, 5.95% H, 6.71% S. $^1H$ NMR spectrum ($CDCl_3$): $CH_3(CO)$ 2.57 s; H(O) 12.76 s; aromatic H on the benzoic acid nucleus: H(2,6) 7.87 d (J=8.7 Hz); H(3,5) 7.01 m.

Example 18

4-(3-(4-(4-Acetyl-3-hydroxy-2-propylphenoxy) butoxy)phenylsulfanyl)benzoic Acid (8)

Methyl ester of the title acid was obtained from methyl 4-(3-(4-bromobutoxy)-phenylsulfanyl)benzoate and 2,4-dihydroxy-3-propylacetophenone as an oily product in 74.2% yield. For $C_{29}H_{32}O_6S$ (508.6) calculated: 68.48% C, 6.34% H, 6.30% S; found: 67.65% C, 6.23% H, 6.72% S. After hydrolysis with a solution of potassium hydroxide and following acidic treatment with hydrochloric acid, the crude product was purified by column chromatography on silica gel to give the title acid (75.0%), m.p. 100–102° C. For $C_{28}H_{30}O_6S$ (494.6) calculated: 68.00% C, 6.11% H, 6.48% S; found: 67.18% C, 6.10% H, 6.50%.

Example 19

Hydrogenmaleate of 2-(4-(2-(1-(4-Chlorobenzyl) piperazin-4-yl)ethoxy)-phenylsulfanyl)benzoic Acid (11)

A mixture of methyl 2-(4-Hydroxyphenylsulfanyl) benzoate (7.8 g, 30.0 mmol), 1-bromo-2-chloroethane (8.6 g, 60.0 mmol), anhydrous potassium carbonate (19.0 g), and 4-methylpentane-2-one (130 ml) was refluxed for 10 h. After addition of a second portion of 1-bromo-2-chloroethane (4.3 g, 30.0 mmol) and anhydrous potassium carbonate (4.7 g), the reflux continued for further 20 h. The hot mixture was filtered, the filtrate was evaporated to dryness under reduced pressure. The crystalline residue was dissolved in chloroform (50 ml), decolorized with charcoal and the filtrate was concentrated under reduced pressure to provide after cooling nearly white crystalline product, (8.4 g, 86.6%), m.p. 109–111° C. For $C_{16}H_{15}ClO_3S$ (322.8) calculated: 59.53% C, 4.68% H, 10.98% Cl, 9.93% S; found: 59.80% C, 4.70% H, 10.90% Cl, 9.98% S.

A mixture of methyl 2-(4-(2-chloroethoxy) phenylsulfanyl)benzoate (7.2 g, 22.0 mmol), 1-(4-chlorobenzyl)piperazine (4.6 g, 22.0 mmol), anhydrous potassium carbonate (10.5 g), potassium iodide (0.2 g) and 4-methylpentane-2-one (120 ml) was refluxed for 20 h (the reaction was monitored by TLC and continued till 1-(4-chlorobenzyl)piperazine was not present in the reaction mixture). The hot mixture was filtered, the filtrate was evaporated to dryness. The residue was purified by column chromatography on silica gel using dichloromethane and chloroform as eluents. Crystallization from a mixture of n-hexane-ether (1:1) provided methyl ester of the title acid (4.2 g, 38.5%), m.p. 106–108° C. For $C_{27}H_{29}ClN_2O_3S$ (497.1) calculated: 65.24% C, 5.88% H, 7.13% Cl, 5.64% N, 6.45% S; found: 65.62% C, 6.19% H, 7.08% Cl, 5.20% N, 6.35% S. $^1H$ NMR spectrum ($CDCl_3$): $CH_3(ester)$ 3.96 s; aromatic H on the phenylsulfanylbenzoic acid moiety: H(6) 8.00 dd (J=2.0, 7.5 Hz); H(3,4,5,3',5') 6.68–7.20 m; aromatic H of 4-chlorobenzyl group 7.28 s. A solution of potassium hydroxide (1.7 g) in water (10 ml) was added to a stirred solution of this ester (3.7 g, 7.4 mmol) in ethanol (40 ml) and the mixture was refluxed for 1 h. The residue after evaporation was dissolved in water and acidified with acetic acid, the mixture was cooled down and the formed precipitate was extracted with chloroform. The extract was dried with sodium sulfate, the residue after evaporation was suspended in ethanol (50 ml) and a solution of maleic acid (1.2 g, 10.0 mmol) in ethanol (10 ml) was added and the mixture was stirred for 8 h at 20° C. The insoluble portion was filtered off, washed with ethanol to provide the title hydrogenmaleate (4.0 g, 90.2%), m.p. 194–196° C. For $C_{26}H_{27}ClN_2O_3S \cdot C_4H_4O_4$ (599.1) calculated: 60.14% C, 5.22% H, 5.92% Cl, 4.68% N, 5.35% S; found: 59.94% C, 5.31% H, 6.01% Cl, 4.51% N, 5.26% S.

Using the procedure described in Example 19, compounds described in Examples 20 and 21 were prepared.

Example 20

Bis-hydrogenmaleate of 2-(3-(3-(1-(4-Chlorobenzyl) piperazin-4-yl)propoxy)-phenylsulfanyl)benzoic Acid (12)

Using the procedure described in Example 19 starting from methyl 2-(3-(3-chloropropoxy)-phenylsulfanyl) benzoate and 1-(4-chlorobenzyl)piperazine, methyl ester of the title acid was obtained as a viscous oil in 74.0% yield. It was identified as its dihydrogenmaleate, m.p. 174–177° C. For $C_{28}H_{31}ClN_2O_3S \cdot 2\ C_4H_4O_4$ (743.2) calculated: 58.17% C, 5.29% H, 4.77% Cl, 3.77% N, 4.31% S; found: 58.29% C, 5.35% H, 4.90% Cl, 3.56% N, 4.35% S. The ester was hydrolyzed with an aqueous-ethanolic solution of potassium hydroxide and the obtained acid was converted to its dihydrogenmaleate (overall yield of 64.2%), m.p. 170–172° C. For $C_{27}H_{29}ClN_2O_3S \cdot 2\ C_4H_4O_4$ (729.2) calculated: 57.65%

C, 5.11% H, 4.86% Cl, 3.84% N, 4.40% S; found: 57.57% C, 5.22% H, 5.10% Cl, 3.70% N, 4.48% S.

Example 21

Dimethanesulfonate of 2-(4-(3-(1-(4-Chlorobenzyl) piperazin-4-yl)-propoxy)phenylsulfanyl)benzoic Acid (13)

Using the procedure described in Example 19 starting from methyl 2-(4-(3-chloropropoxy-phenylsulfanyl) benzoate and 1-(4-chlorobenzyl)piperazine, methyl ester of the title acid was obtained 87.9% yield. m.p. 109–111° C. (ethanol). For $C_{28}H_{31}ClN_2O_3S$ (511.0) calculated: 65.80% C, 6.11% H, 6.97% Cl, 5.48% N, 6.27% S; found: 66.05% C, 6.19% H, 7.20% Cl, 5.43% N, 6.30% S. $^1$H NMR spectrum (CDCl$_3$): CH$_3$(ester) 3.94 s; aromatic H on the phenylsulfanyl)benzoic acid moiety: H(3,4,5) 8.00 6.70–7.20 m;, H(6) 8.00 dd, J=2.0, 9.0 Hz; H(2',6') 7.98 d, J=9 Hz; aromatic H of 4-chlorobenzyl group 7.26 s.

The ester was saponified and after acidification with acetic acid the title acid was obtained in 81.2% yield, m.p. 214–216° C. This compound (4.2 g, 17.0 mmol) was dissolved in ethanol (20 ml) and a solution of methanesulfonic acid (1.6 g, 17.0 mmol) in ethanol (20 ml) was added. This solution was diluted under stirring with ether (80 ml), cooled down and the formed precipitate was filtered to give the title dimethanesulfonate (4.2 g, 71.7%), m.p. 146–148° C. For $C_{27}H_{29}ClN_2O_3S$. 2 $CH_4O_3S$ (689.1) calculated: 50.53% C, 5.41% H, 5.14% Cl, 4.06% N, 13.96% S; found: 50.23% C, 5.48% H, 5.21% Cl, 3.71% N, 13.89% S.

Example 22

Bis-hydrogenmaleate of Methyl 2-(3-(3-(1-(2-hydroxyethyl)piperazin-4-yl)-propoxy)phenyl-sulfanyl)benzoate (15)

A mixture of methyl 2-(3-(3-chloropropoxy) phenylsulfanyl)benzoate (7.6 g, 22.0 mmol), 1-(2-hydroxyethyl)piperazine (3.0 g, 22.0 mmol), anhydrous potassium carbonate (8.3 g), sodium iodide (0.5 g) and dimethylformamide (50 ml) was stirred at 90–95° C. for 8 h. The mixture was cooled down and poured into ice cold water (300 ml) and the mixture was extracted with chloroform (3×100 ml). The extract was dried with magnesium sulfate, the solvent was evaporated and the oily residue (9.1 g) was dissolved in hot ethanol (25 ml). A concentrated solution of maleic acid (4.9 g, 42.0 mmol) in ethanol was added to the solution, the mixture was cooled an the formed precipitate was filtered and washed with cold ethanol to give crude dihydrogenmaleate (11.3 g). Crystallization from ethanol provided the title compound (9.8, 66.4%), m.p. 151–153° C. For $C_{23}H_{30}N_2O_4S$. 2 $C_4H_4O_4$ (662.6) calculated: 56.18% C, 5.78% H, 4.23% N, 4.84% S; found: 56.32% C, 5.60% H, 4.07% N, 4.83% S.

Example 23

4-(4-Quinoline-2-methoxy)phenylsulfanyl)benzoic Acid (16)

A stirred mixture of methyl 4-(4-hydroxyphenylsulfanyl) benzoate (6.0 g, 23.0 mmol), 2-chloromethylquinoline (4.4 g, 25.0 mmol), anhydrous potassium carbonate (10.0 g), sodium iodide (0.1 g), and butan-2-one (80 ml) was refluxed for 8 h. The hot mixture was filtered, the filtrate cooled to 5° C. and the formed precipitate was filtered of to give methyl ester of the title acid (6.0 g), m.p. 126–128. For $C_{24}H_{19}NO_3S$ (401.5) calculated: 71.80% C, 4.77% H, 3.49% N, 7.99% S; found: 71.38% C, 4.81% H, 3.23% N, 7.99% S. The mother liquor was evaporated to dryness, the residue boiled with methanol (100 ml) to provide, after cooling, another crop of the ester (2.2 g), m.p. 125–127. The overall yield achieved is 8.2 g (82.1%).

This ester (5.7 g, 14.2 mmol) was suspended in ethanol (40 ml), a solution of potassium hydroxide (2.3 g) in water (15 ml) was added and the mixture was boiled to dissolved the insoluble part. After 15 min, the formed solution was evaporated to dryness and the residue (nearly white) was dissolved in boiling water (250 ml). The solution was decolorized with charcoal, the clear filtrate was acidified with acetic acid, the formed precipitate was filtered and suspended in a mixture of 2-propanol (100 ml) and water (5 ml) and dissolved under reflux. The product precipitated after cooling to 40° C., it was filtered and washed with 2-propanol to give the title acid (5.2 g, 94.4%), m.p. 204–206° C. For $C_{23}H_{17}NO_3S$ (387.5) calculated: 71.30% C, 4.42% H, 3.61% N, 8.28% S; found: 71.15% C, 4.55% H, 3.38% N, 8.29% S. $^1$H NMR spectrum (DMSO-d6, 60° C.): CH$_2$(O) 5.43 s; aromatic H on the benzoic acid nucleus: H(2,6) 7.83 d, J=8.7 Hz; H(3,5) 7.12 m.

Using the procedure described in Example 23, acids described in Examples 24–27 were prepared.

Example 24

2-(3-(Quinoline-2-ylmethoxy)phenylsulfanyl) benzoic Acid (17)

Using the procedure described in Example 23 starting from 2-chloromethyiquinoline and methyl 2-(3-hydroxyphenylsulfanyl)benzoate, methyl ester of the title acid was obtained as red-brown crystals in nearly quantitative yield, m.p. 52–55° C. An analytical sample was further purified by crystallization from a mixture of ethanol and ether. For $C_{24}H_{19}NO_3S$ (401.5) calculated: 71.80% C, 4.77% H, 3.49% N, 7.99% S; found: 71.83% C, 4.76% H, 3.18% N, 7.75% S.

The crude ester was hydrolyzed and after acidification, the product was crystallized from 2-butanone and n-hexane to yield the title acid (60.9%), m.p. 169–171° C. For $C_{23}H_{17}NO_3S$ (387.5) calculated: 71.30% C, 4.42% H, 3.61% N, 8.28% S; found: 71.06% C, 4.50% H, 3.38% N, 8.13% S.

Example 25

2-(4-(Quinoline-2-ylmethoxy)phenylsulfanyl) benzoic Acid (19)

Using the procedure described in Example 23 starting from 2-chloromethylquinoline and methyl 2-(4-hydroxyphenylsulfanyl)benzoate, the crude methyl ester was obtained and its further crystallization from methanol provided methyl ester of the title acid in 92.1% yield, m.p. 134–136° C. For $C_{24}H_{19}NO_3S$ (401.5) calculated: 71.80% C, 4.77% H, 3.49% N, 7.99% S; found: 71.53% C, 4.80% H, 3.46% N, 8.30% S.

The ester was hydrolyzed and after acidification, the product was crystallized from 2-butanone to yield the title acid (52.3%), m.p. 208–210° C. For $C_{23}H_{17}NO_3S$ (387.5) calculated: 71.30 % C, 4.42% H, 3.61% N, 8.28% S; found: 71.08% C, 4.61% H, 3.89% N, 8.06% S. $^1$H NMR spectrum (DMSO-d6, 60° C.): CH$_2$(O) 5.41 s; aromatic H on the benzoic acid nucleus: H(3,5) 8.38 d, J=8.4 Hz; H(4,6) 7.01–8.10 m.

Example 26

2-(3-(6-Chloroquinoline-2-ylmethoxy) phenylsulfanyl)benzoic Acid (20)

Using the procedure described in Example 23 starting from 6-chloro-2-chloromethylquinoline and methyl 2-(3-hydroxyphenylsulfanyl)benzoate, crude methyl ester was obtained and after crystallization from methanol provided methyl ester of the title acid in 91.9% yield, m.p. 98–100° C. For $C_{24}H_{18}ClNO_3S$ (435.9) calculated: 66.13% C, 4.16% H 8.13% Cl, 3.21 N, 7.36% S; found: 65.93% C, 4.27% H, 8.30% Cl, 3.09% N, 7.17 % S; $^1H$ NMR ($C^2HCl_3$): $CH_3$ (OCO) 3.95 s $CH_2\{O\}$ 5.36 s.

The ester was saponified and after acidification, the crude product was purified through ammonium salt to yield the title acid (37.7%), m.p. 209–211° C. For $C_{23}H_{16}ClNO_3S$ (421.9) calculated: 65.48% C, 3.82% H, 8.40% Cl, 3.32% N, 7.60% S; found: 65.56% C, 3.98% H, 8.62% Cl, 3.35% N, 7.56% S. $^1H$ NMR spectrum (DMSO-$d_6$): 5.35 s; aromatic H on the benzoic acid nucleus: H(3) 6.89 m, H(4,5) 7.10 m, H(6) 7.78 m.

Example 27

4-(4-(6-Chloroquinoline-2-ylmethoxy) phenylsulfanyl)benzoic Acid (22)

Using the procedure described in Example 23 starting from 6-chloro-2-chloromethylquinoline and methyl 4-(4-hydroxyphenylsulfanyl)benzoate, methyl ester of the title acid was obtained in 91.3% yield, m.p. 130–132° C. For $C_{24}H_{18}ClNO_3S$ (435.9) calculated: 66.13% C, 4.16% H, 8.13% Cl, 3.21% N, 7.36% S; found: 65.84% C, 4.14% H, 8.29% Cl, 3.60% N, 7.16% S. $^1H$ NMR spectrum ($C^2HCl_3$): $CH_3$(ester) 3.87 s; $CH_2$(O) 5.38 s; aromatic H on the benzoic acid nucleus: H(2,6) 7.85 d, J=8.5 Hz; H(3,5) 7.09 d, J=8.5 Hz.

The ester was hydrolyzed under alkaline conditions and after acidification, the product was crystallized from dimethylformamide to yield the title acid (93.0%), m.p. 232–235° C. For $C_{23}H_{16}ClNO_3S$ (421.9) calculated: 65.48% C, 3.82% H, 8.40% Cl, 3.32% N, 7.60% S; found: 65.31% C, 3.91% H, 8.34% Cl, 3.60% N, 7.52% S. $^1H$ NMR spectrum (DMSO-$d_6$, 60° C.): $CH_2$(O) 5.37 s; aromatic H on the benzoic acid nucleus: H(2,6) 7.82 d, J=8.2 Hz; H(3,5) 7.16 d, J=8.2 Hz.

Example 28

Tromethammonium salt of 2-(3-(6-Chloroquinoline-2-ylmethoxy)phenyl-sulfanyl)benzoic Acid (23)

Acid 20 (3.36 g, 8.0 mmol) and tris-(hydroxymethyl)methylamine (1.7 g, 14.0 mmol) were dissolved in dimethyl sulfoxide (25 ml), the clear slightly brown solution after 10 min at 20° C. was poured into ice-cold water (120 ml) and left to stand overnight in a refrigerator. The formed precipitate was filtered, washed with water and dried to give the title salt (3.5 g, 79.9%), m.p. 177–179° C. For $C_{27}H_{27}ClN_2O_6S$ (543.0) calculated: 59.72% C, 5.01% H, 6.53% Cl, 5.16% N, 5.89% S; found: 59.70% C, 4.96% H, 6.66% Cl, 5.04% N, 6.18% S.

Example 29

Tromethammonium salt of 4-(4-(Quinoline-2-ylmethoxy)phenylsulfanyl)benzoic Acid (24)

Using the procedure described in Example 28, from acid 16 and tris-(hydroxymethyl)methylamine, the title salt was prepared in 91.6% yield, m.p. 195–197° C. For $C_{27}H_{28}N_2O_6S$ (508.6) calculated: 63.76% C. 5.55% H, 5.50% N, 6.30% S; found: 63.61% C, 5.51% H, 5.17% N, 6.35% S.

Example 30

Methyl 2-(4-Hydroxyphenylsulfanyl)phenylacetate

2-(4-Methoxyphenylsulfanyl)benzyl alcohol

A mixture of a 60% solution of Na bis-(2-methoxyethoxy) aluminum hydride (85.0 g) and toluene (120 ml) was added dropwise during 1 h to a stirred suspension of 2-(4-methoxyphenylsulfanyl)benzoic acid (33.4 g, 0.128 mol) in toluene (270 ml) under nitrogen atmosphere. Temperature of the reaction mixture was allowed to reach 50° C., then the mixture was cooled down to 20° C. and the mixture was stirred for 5 h. Then a 10% solution of sodium hydroxide (50 ml) was added, the toluene layer was separated and successively washed with a 5% solution of sulfuric acid (50 ml) and water (2×50 ml). An oily residue after evaporation of toluene (31.2 g, 99.2%) was used for the next step without further purification.

2-(4-Methoxyphenylsulfanyl)benzyl chloride

A solution of the crude alcohol from the previous step (31.1 g, 0.126 mol) and pyridine (5.1 ml) in toluene (200 ml) was cooled to −5° C. and then a solution of thionyl chloride (16.7 g, 0.14 mol) was slowly added under stirring so that the temperature did not exceed 0° C. When the addition was complete, the mixture was stirred at 80° C. for 1.5 h and then cooled to 20° C. The cold mixture was successively washed with ice-cold water (50 ml), a 5% solution of $NaHCO_3$ (2×50 ml) and water (50 ml) and dried. The crude benzyl chloride obtained after evaporation (29.0 g, 86.8%) was used for the next step without further purification. A sample for elemental analysis was crystallized from diisopropyl ether, m.p. 80–82° C. For $C_{14}H_{13}ClOS$ (264.8) calculated: 63.51% C, 4.95% H, 13.39% Cl, 12.11% S; found: 63.43% C, 5.05% H, 13.16% Cl, 12.10% S.

2-(4-Methoxyphenylsulfanyl)phenylacetonitrile

A solution of the crude benzyl chloride from the previous step (29.0 g, 0.11 mol) was dissolved at 80° C. in ethanol (180 ml), the stirred solution was cooled to 50° C. and at this temperature a solution of sodium cyanide (8.6 g, 0.175 mol) in water (35 ml) was added. The mixture was stirred at 80° C. for 7 h, ethanol was evaporated under reduced pressure, water (50 ml) was added and the mixture was extracted with chloroforn (2×100 ml). The combined extracts were washed with saturated solution of sodium chloride (2×25 ml) and dried with sodium sulfate. The residue after evaporation was mixed with ethanol (35 ml) and the crystals were isolated by suction and washed with cold ethanol to provide the required nitrile (24.2 g, 86.4%) used in the next step.

2-(4-Methoxyphenylsulfanyl)phenylacetic acid: A solution of potassium hydroxide (25.9 g, 0.463 mol) in water (60 ml) was added to a stirred solution of 2-(4-methoxyphenylsulfanyl)phenylacetonitrile (31.2 g, 0.119 mol) in ethanol (185 g) and the mixture was refluxed for 7 h. Then the mixture was evaporated to dryness, the residue was dissolved in water (100 ml), the solution was filtered with charcoal to give a clear solution which was acidified to pH 1 with hydrochloric acid under cooling. The separated oil slowly provided a crystalline material which was filtered off and washed with water to neutral reaction of the washings.

This procedure yielded 27.3 g (84.3%) of the required acid, m.p. 102–105° C.

2-(4-Hydroxyphenylsulfanyl)phenylacetic acid

A mixture of the acid from the previous step (22.9 g, 0.084 mol) and pyridine hydrochloride (69.3 g, 0.6 mol) was stirred at 240° C. under nitrogen atmosphere for 20 min. After cooling to 80° C., water (250 ml) was added, the mixture was cooled to 5° C. and after 2 h the formed precipitate was filtered and washed with water to give the requited acid (19.4 g, 89.3%), m.p. 183–185° C. For $C_{14}H_{12}O_3S$ (260.3) calculated 64.60% C, 4.65% H, 12.32% S; found: 64.35% C, 4.82% H, 12.03% S. Methyl 2-(4-hydroxyphenylsulfanyl)phenylacetate: Concentrated sulfuric acid (2 ml) was added to a solution of the acid from the previous step (19.4 g, 0.075 mol) in methanol (210 ml) and the mixture was refluxed for 10 h. Then the mixture was concentrated to half of its volume and toluene (100 ml) and water (200 ml) was added. Crystalline product formed after vigorous stirring was filtered and washed with water to provide the required methyl ester (14.2 g, 69.6%), m.p. 126 128° C. For $C_{15}H_{14}O_3S$ (274.3) calculated: 65.69% C, 5.15% H, 11.67% S; found: 65.40% C, 5.35% H, 11.39% S.

Using the procedure described in Example 30, methyl esters described in Examples 31–33 were prepared.

Example 31

Methyl 4-(4-Hydroxyphenylsulfanyl)phenylacetate 4-(4-Methoxyphenylsulfanyl)benzoic acid was reduced with sodium bis-(methoxyethoxy)-aluminum hydride to provide in 51.5% yield 4-(4-methoxyphenylsulfanyl)benzyl alcohol. Its reaction with thionyl chloride provided in 93.3% yield the corresponding benzyl chloride which treated with sodium cyanide provided in 71.1% 4-(4-methoxyphenylsulfanyl)phenylacetonitrile. Alkaline hydrolysis provided after work-up 47.5% yield of 4-(4-methoxyphenyl-sulfanyl)phenylacetic acid, m.p. 85–87° C. Demethylation of this acid with pyridine hydrochloride provided in 98.0% yield 4-(4-hydroxyphenylsulfanyl) phenylacetic acid, m.p. 83–85° C., which was esterified with methanol in the presence of 4-toluenesulfonic acid to give the required ester as an oil. For $C_{15}H_{14}O_3S$ (274.3) calculated: 11.67% S; found: 11.49%. $^1H$ NMR spectrum ($CDCl_3$): H(O) 5.63 bs; $CH_2$ 3.58 s; aromatic H on the phenolic nucleus: H(2,6) 6.76 d, J=8.8 Hz; H(3,5) 7.33 d, J=8.8 Hz.

Example 32

Methyl 2-(3-Hydroxyphenylsulfanyl)phenylacetate 2-(3-Methoxyphenylsulfanyl)benzoic acid was reduced with sodium bis-(methoxyethyoxy)-aluminum hydride to provide in 87.6% yield 2-(3-methoxyphenylsulfanyl)benzyl alcohol. This compound was without purification treated with thionyl chloride to provide in 91.0% yield 2-(3-methoxyphenylsulfanyl)benzyl chloride which treated with sodium cyanide provided nearly quantitatively 2-(3-methoxyphenylsulfanyl)phenylacetonitrile. Alkaline hydrolysis of this crude nitrile provided after work-up 65.1% yield of 2-(3-methoxyphenylsulfanyl)phenylacetic acid, m.p. 63–65° C. Corresponding 4-(4-hydroxyphenylsulfanyl)phenylacetic acid, m.p. 163–165° C., was obtained in 76.5% yield. For $C_{14}H_{12}O_3S$ (260.3) calculated: 64.60% C, 4.65% H, 12.32% S; found: 64.30% C, 4.85% H, 12.10% S. This acid was esterified with methanol in the presence of sulfuric acid to give the required ester in 78.9% yield, m.p. 54–56° C. For $C_{15}H_{14}O_3S$ (274.3) calculated: 65.69% C, 5.15% H, 11.67% S; found: 64.79% C, 5.25% H, 11.45% S. $^1H$ NMR spectrum ($CDCl_3$): H(O) 5.60 bs; $CH_2$ 3.85 s; aromatic H on the phenolic nucleus: H(2) 6.54 dd, J=1.6, 2.5 Hz; H(5) 7.08 dd, J=7.9, 8.2 Hz; H(6) 6.72 ddd, J=1.0, 1.6, 7.9 Hz.

Example 33

Methyl 2-(4-Hydroxyphenylsulfanyl)phenylacetate 2-(4-Methoxyphenylsulfanyl)benzoic acid was reduced with sodium bis-(methoxyethoxy)-aluminum hydride to provide in 84.7% yield 2-(4-methoxyphenylsulfanyl)benzyl alcohol. This compound was without purification treated with thionyl chloride to provide in 95.0% yield 2-(4-methoxyphenylsulfanyl)benzyl chloride, m.p. 76–78° C. For $C_{14}H_{13}ClOS$ (264.8) calculated: 63.51% C, 4.95% H, 13.39% Cl, 12.11% S; found: 63.43% C, 5.05% H, 13.16% Cl, 12.10% S. This compound was treated with sodium cyanide to provide in 94.6% yield 2-(4-methoxyphenylsulfanyl)phenylacetonitrile, m.p. 65–67° C. Alkaline hydrolysis of this nitrile provided after work-up 69.7% yield of 2-(4-methoxyphenyl-sulfanyl)phenylacetic acid, m.p. 177–179° C. Demethylation with pyridine hydrochloride provided in 82.5% yield 2-(4-hydroxyphenylsulfanyl)phenylacetic acid, m.p. 163–165° C. This acid was esterified with methanol in the presence of sulfuric acid to give the required ester in 77.8% yield, m.p. 126–128° C. For $C_{15}H_{14}O_3S$ (274.3) calculated: 65.69% C, 5.15% H, 11.67% S; found: 65.17% C, 5.14% H, 11.69% S. $^1H$ NMR spectrum ($CDCl_3$): H(O) 5.17 bs; $CH_2$ 3.85 s; aromatic H on the phenolic nucleus: H(3,5) 6.73 d, J=8.8 Hz.

Example 34

Methyl 2-(3-(3-Chloropropoxy)phenylsulfanyl) phenylacetate

A stirred mixture of methyl 2-(3-hydroxyphenylsulfanyl) phenylacetate (4.1 g, 14.9 mmol) and 1-bromo-3-chloropropane (13.0 g, 60 mmol), anhydrous potassium carbonate (5.2 g) and butan-2-one (60 ml) was refluxed for 9 h. The hot mixture was filtered, the filtrate was evaporated and the oily residue (5.04 g, 65.4%) was used without further purification for the preparation of compound 27. For $C_{18}H_{19}ClO_3S$ (350.9) calculated: 10.10% Cl, 0.00% Br, 9.14% S; found: 9.38% Cl, 2.82% Br, 8.85% S. $^1H$ NMR spectrum ($CDCl_3$): $CH_2(COO)$ 3.83 s; $CH_3$ 3.58 s; $CH_2(O)$ 3.98 t, J=6.3 Hz; $CH_2(Cl)$ 3.65 t, J=6.3 Hz.

Example 35

Methyl 2-(4-(3-Chloropropoxy)phenylsulfanyl) phenylacetate

Using the procedure described in Example 34, methyl 2-(4-hydroxyphenylsulfanyl)phenyl-acetate and 1-bromo-3-chloropropane provided 73.3% yield of the title ester, m.p. 48–51° C. For $C_{18}H_{19}ClO_3S$ (350.9) calculated: 61.62% C, 5.46% H, 10.10% Cl, 9.14% S; found: 61.12% C, 5.44% H, 10.15% Cl, 9.13% S. $^1H$ NMR spectrum ($CDCl_3$): $CH_2$(COO) 3.84 s; $CH_3$ 3.67 s; $CH_2(O)$ 4.09 t, J=6.0 Hz; $CH_2(Cl)$ 3.73 t, J=6.0 Hz.

Example 36

2-(4-(3-(4-Acetyl-3-hydroxy-2-propylphenoxy) propoxy)phenylsulfanyl)phenylacetic Acid (25)

A stirred mixture of methyl 2-(4-hydroxyphenylsulfanyl) phenylacetate (4.0 g, 14.6 mmol), 4-(3-chloropropoxy)-2- hydroxy-3-propylacetophenone (3.9 g, 14.6 mmol), anhydrous potassium carbonate (6.5 g), potassium iodide (0.5 g) and butan-2-one (125 ml) was refluxed for 8 h. Then further potassium carbonate (2.0 g) was added and the reflux continued for additional 30 h. The hot mixture was filtered, the filtrate was evaporated under reduced pressure to dryness. The residue was mixed with ether (30 ml), cooled and left in a refrigerator at 5° C. for 12 h. Then the formed crystalline portion was filtered to give methyl ester of the title acid (5.0 g, 67.3%), m.p. 79–82° C. An analytical sample was crystallized from ether, m.p. 80–82° C. For $C_{29}H_{32}O_6S$ (509.1) calculated: 68.48% C, 6.34% H, 6.30% S; found: 68.07% C, 6.36% H, 6.16%. $^1$H NMR spectrum (CDCl$_3$): CH$_2$(COO) 3.82 s; CH$_3$(OCO) 3.64 s; CH$_3$(CO) 2.50 s; OH 12.77 s; CH$_2$(O) 4.19 t, J=6.3 Hz+4.13 t, J=6.3 Hz.

A solution of potassium hydroxide (2.0 g) in water (15 ml) was added to a stirred solution of this ester (4.6 g, 9.0 mmol) in ethanol (55 ml) and the mixture was refluxed for 30 min. The solution after evaporation of ethanol was diluted with water (50 ml) and acidified to pH 1 with hydrochloric acid. The formed viscous oil was extracted with ether (2×35 ml), dried with magnesium sulfate and evaporated. The crude product was crystallized from 70% aqueous methanol (50 ml) to give the title acid (3.3 g, 75.0%), m.p. 123–124° C. For $C_{28}H_{30}O_6S$ (494.6) calculated: 68.00% C, 6.11% H, 6.48% S; found: 68.26% C, 6.07% H, 6.14% S. $^1$H NMR spectrum (CDCl$_3$, 60° C.): CH$_1$(COO) 3.87 s;, CH$_2$(O) 4.21 t, J=6.0 Hz+4.15 t, J=6.0 Hz; OH 12.66 s.

Using the procedure described in Example 36, acid 26 described in Example 37 was prepared.

Example 37

2-(4-(4-(4-Acetyl-3-hydroxy-2-propylphenoxy) butoxy)phenylsulfanyl)phenylacetic Acid (26)

From methyl 2-(4-hydroxyphenylsulfanyl)phenylacetate and 4-(4-bromobutoxy)-2-hydroxy-3-propylacetophenone was prepared in 96.5% yield the corresponding methyl ester, m.p. 76–78° C. (ether). $^1$H NMR spectrum (CDCl$_3$): CH$_3$(OCO) 3.66 s; CH$_2$(COO) 3.83 s; CH$_3$(CO) 2.55s; CH$_2$(O) 4.08 bt+4.01 bt.

Hydrolysis of this ester provided the title acid 26 in 73.6% yield, m.p. 131–133° C. For $C_{29}H_{32}O_6S$ (508.6) calculated: 68.48% C, 6.34% H, 6.30% S; found: 68.25% C, 6.43% H, 6.23% S. $^1$H NMR spectrum (CDCl$_3$): CH$_2$(COO) 3.88 s; CH$_3$(CO) 2.55 s; CH$_2$(O) 4.10 bt; OH 12.72 s.

Example 38

Dihydrogenmaleate of 2-(3-(3-(1-(4-Chlorobenzyl) piperazin-4-yl)-propoxy)phenylsulfanyl)phenylacetic Acid (28)

A mixture of methyl 2-(3-(3-chloropropoxy) phenylsulfanyl)phenylacetate (4.1 g, 10.0 mmol), 1-(4-chlorobenzyl)piperazine (2.1 g, 10.0 mmol), anhydrous sodium carbonate (7.0 g), sodium iodide (0.4 g) and dimethylformamide (40 ml) was stirred at 100° C. for 4 h. The mixture was poured onto an ice-water mixture (200 g), the mixture was extracted with chloroform (3×50 ml). The combined extracts were dried with sodium sulfate and the residue after evaporation was purified by column chromatography on silica gel using toluene with 1.5% of methanol as eluent to give 4.7 g of the methyl ester (89.5%). $^1$H NMR spectrum (CDCl$_3$): CH$_3$(OCO) 3.50 s; CH$_2$(COO) 3.35 s; CH$_2$(O) 3.83 t, J=6.6 Hz; CH$_2$ (piperazine) 2.37 m.

A solution of potassium hydroxide (4.0 g) in water (10 ml) was added to a stirred solution of this oily ester (4.7 g, 9.0 mmol) in ethanol (40 ml) and the mixture was refluxed for 2 h. The residue after evaporation of ethanol under reduced pressure was diluted with water (30 ml) and separated oil was extracted with ether. The water layer was acidified with acetic acid to pH 4.5 and the formed semisolid material was extracted with chloroform (3×35 ml) and the extract was dried with sodium sulfate and evaporated. $^1$H NMR spectrum (CDCl$_3$): COOH 7.7 bs; CH$_2$(COO) 3.49 s; CH$_2$(O) 3.87 t, J=6.0 Hz; CH$_2$ (piperazine) 3.80 s. The residue was dissolved in ethanol (25 ml) and a solution of maleic acid (1.9 g, 16.4 mmol) in ethanol (10 ml) was added and the mixture was left in a refrigerator overnight. The insoluble portion was filtered off to provide the title dihydrogenmaleate (4.25 g, 74.6%), m.p. 174–176° C. For $C_{28}H_{31}ClN_2O_3S.2$ $C_4H_4O_4.0.5$ $H_2O$ (636.2) canculated: 57.48% C, 5.36% H, 4.72% Cl, 3.72% N, 4.26% S; found: 57.47% C, 5.36% H, 4.88% Cl, 3.49% N, 4.43% S.

Example 39

2-(4-(Quinoline-2-ylmethoxy)phenylsulfanyl) phenylacetic Acid (29)

A stirred mixture of methyl 2-(4-hydroxyphenylsulfanyl) phenylacetate (5.0 g, 18.0 mmol), 2-chloromethylquinoline (3.2 g, 18.0 mmol), anhydrous potassium carbonate (6.5 g), potassium iodide (0.2 g), and butan-2-one (70 ml) was refluxed for 8 h. The hot mixture was filtered, the filtration cake was washed with boiling butan-2-one (2×15 ml) and the filtrate was again filtered with charcoal. The solution was evaporated under reduced pressure. The crystalline residue was mixed with methanol (15 ml) and left to stand overnight in a refrigerator. The crystalline methyl ester of the title acid was filtered (5.9 g, 80.8%), m.p. 100–102. $^1$H NMR spectrum (CDCl$_3$): CH$_3$(OCO) 3.64 s; CH$_2$(COO) 3.83 s; CH$_2$(O) 5.36 s; aromatic H of the quinoline nucleus: H(3) 7.64 d, J=8.8 Hz; H(4) 8.18 d, J=8.8 Hz; H(5) 7.82 dd, J=1.3, 8.5 Hz; H(6) 7.54 m; H(7) 7.73 m; H(8) 8.08 d, J=8.5 Hz; This ester (5.9 g, 14.2 mmol) was suspended in ethanol (75 ml), a solution of potassium hydroxide (1.5 g, 27 mmol) in water (10 ml) was added and the mixture was refluxed 30 min. Then ethanol was evaporated under reduced pressure, the mixture was diluted with water (100 ml) and the cloudy solution was filtered with charcoal. The filtrate was acidified with acetic acid to pH 4.5, the mixture was cooled to 5° C. and the formed precipitate was filtered. The crude product was purified by crystallization from ethanol (120 ml) to give the title acid (3.0 g, 52.6%), m.p. 179–181° C. For $C_{24}H_{19}NO_3S$ (401.5) calculated: 71.80% C, 71.80% C, 4.77% H, 3.49% N, 7.99% S; found: 71.67% C, 4.94% H, 3.41% N, 7.77% S. $^1$H NMR spectrum (DMSO-d6, 60° C.): CH$_2$(COO) 3.77 s; CH$_2$(O) 5.38 s; aromatic H of the quinoline nucleus: H(3) 7.67 d, J=8.2 Hz; H(4) 8.40 d, J=8.2 Hz; H(5) 8.03 d, J=8.5 Hz; H(6) 7.78 m; H(7) 7.61 m; H(8) 7.98 dd, J=0.9, 8.5 Hz;

Using the procedure described in Example 39, acids described in Examples 40–42 were prepared.

Example 40

4-(4-(Quinoline-2-ylmethoxy)phenylsulfanyl) phenylacetic Acid (30)

Using the procedure described in Example 39, starting from methyl 4-(4-hydroxyphenyl-sulfanyl)phenylacetate and 2-chloromethylquinoline, the crude methyl ester of the title acid was prepared in nearly quantitative yield. $^1$H NMR spectrum (CDCl$_3$): CH$_3$(OCO) 3.66 s; CH$_2$(COO) 3.55 s; CH$_2$(O) 5.37 s; aromatic H of the quinoline nucleus: H(3) 7.67 d, J=8.5 Hz; H(4) 8.17 d, J=8.5 Hz; H(5) 7.81 dd, J=1.6, 8.2 Hz; H(6) 7.53 m; H(7) 7.72 m; H(8) 8.08 dd, J=1.3, 8.5 Hz. The oily ester was without further purification hydrolyzed to the title acid (78.9%), m.p. 176–178° C. (ethanol). For C$_{24}$H$_{19}$NO$_3$S (401.5) calculated: 71.80% C, 4.77% H, 3.49% N, 7.99% S; found: 72.13% C, 4.89% H, 3.40% N, 7.82% S. $^1$H NMR spectrum (CDCl$_3$): CH$_2$(COO) 3.54 s; CH$_2$(O) 5.39 s; aromatic H of the quinoline nucleus: H(3) 9.68 d, J=8.5 Hz; H(4) 8.40 d, J=8.5 Hz; H(5) 7.99 dd, J=1.3, 8.5 Hz; H(6) 7.62 m; H(7) 7.78 m; H(8) 8.02 d, J=8.5 Hz.

Example 41

2-(3-(6-Chloroquinoline-2-ylmethoxy)phenylsulfanyl)phenylacetic Acid (31)

Using the procedure described in Example 39, starting from methyl 2-(3-hydroxyphenyl-sulfanyl)phenylacetate and 6-chloro-2-chloromethylquinoline, the methyl ester of the title acid was prepared in 92.0% yield. $^1$H NMR spectrum (CDCl$_3$): CH$_3$(OCO) 3.59 s; CH$_2$(COO) 3.79 s; CH$_2$(O) 5.23 s; aromatic H of the quinoline nucleus: H(3) 7.56 d, J8.2 Hz; H(4) 7.99 d, J=8.2 Hz; H(5) 7.73 d, J=2.5 Hz; H(7) 7.61 dd, J=2.5, 8.8 Hz; H(8) 7.95 d, J=8.8 Hz. The oily ester was without further purification hydrolyzed to the title acid (56.0%), m.p. 167–169° C. For C$_{24}$H$_{18}$ClNO$_3$S.H$_2$O (453.9) calculated: 63.50% C, 4.44% H, 7.81% Cl, 3.08% N, 7.06% S; found: 63.67% C, 4.53% H, 8.03% Cl, 2.95% N, 7.02% S. $^1$H NMR spectrum (DMSO-d6, 60° C.): CH$_2$(COO) 3.72 s; CH$_2$(O) 5.29s; aromatic H of the quinoline nucleus: H(3) 7.64 d, J=8.5 Hz; H(4) 8.35 d, J=8.5 Hz; H(5) 8.10 d, J=2.2 Hz; H(7) 7.77 dd, J=2.2, 9.1 Hz; H(8) 8.01 d, J=9.1 Hz.

Example 42

2-(4-(6-Chloroquinoline-2-ylmethoxy)phenylsulfanyl)phenylacetic Acid (32)

Using the procedure described in Example 39, starting from methyl 2-(4-hydroxyphenyl-sulfanyl)phenylacetate and 6-chloro-2-chloromethylquinoline and prolonging the reaction time to 12 h, the miethyl ester of the title acid was prepared in 88.9 % yield; m.p. 90–92° C. $^1$H NMR spectrum (CDCl$_3$): CH$_3$(OCO) 3.65 s; CH$_2$(COO) 3.84 s; CH$_2$(O) 5.33 s; aromatic H of the quinoline nucleus: H(3,7) 7.66 m; H(4,8) 8.09 d, J=8.5 Hz+8.00 d, J=8.87 Hz; H(5) 7.80 d, J=2.5 Hz. The crude ester was without further purification hydrolyzed to the title acid, the crude product was crystalized from a mixture dimethylformamide—water (5:1) and then digested with boiling ethanol to give the product in 63.9% yield, m.p. 205–207° C. For C$_{24}$H$_{18}$ClNO$_3$S (435.9) calculated: 66.12% C, 4.16% H, 8.13% Cl, 3.21% N, 7.36% S; found: 66.25% C, 4.13% H, 8.25% Cl, 3.12% N, 7.15% S. $^1$H NMR spectrum (DMSO-d6): CH$_2$(COO) 3.79 s; CH$_2$(O) 5.36 s; aromatic H of the quinoline nucleus: H(3) 7.71 d, J=8.5 Hz; H(4) 8.36 d, J=8.5 Hz; H(5) 8.07 d, J=2.5 Hz; H(7) 7.74 dd (overlapped) with H(3)); H(8) 8.02 d, J=9.1 Hz.

Example 43

Preparation of Hard Gelatin Capsules

Hard gelatin capsules can be prepared from mixtures of the following composition:

| | |
|---|---|
| Active ingredient | 15 parts |
| *Amylum anaylis* | 4 parts |
| *Sacharum lactis* | 37 parts |
| *Silicii oxydum* | 0.3 part |
| *Magnesii steraras* | 0.7 part |

Example 44

Preparation of Coated Tablets

Lenticular cores prepared from mixtures from Example 43 are coated with a water dispersion of the following composition:

| | |
|---|---|
| Hypromelosum | 67.13 part |
| Macrogolum 6000 | 9.7 part |
| Pigment | 2.23 part |
| Antifoaming additive | 0.87 part |
| Aqua purificata | q.s. |

TABLE I

Biological properties in vitro of derivatives of hydroxyarylsulfanylbenzoic acids (1, n = 0)

| Compound | | Position | | | Inh. of LTB$_4$ biosynth. | | Inh. of LTB$_4$ rec. binding | | Inh. of LTD$_4$ rec. binding | | Antiox. effect |
|---|---|---|---|---|---|---|---|---|---|---|---|
| No. | Z$^a$ | M | —S— | COOH | X | %/µg | IC$_{50}$$^b$ | %/µM | IC$_{50}$$^c$ | %/µM | IC$_{50}$$^c$ | %/100 µg |
| 1 | RES | 2 | 4 | 4 | H | 100/30 | 3.5 | 61/20 | 17 | 98/100 | 10.8 | 54 |
| 2 | RES | 2 | 3 | 4 | H | 100/30 | 0.8 | 98/20 | 5.2 | 88/100 | 26.1 | 41 |
| 3 | RES | 3 | 4 | 4 | H | 100/30 | 0.48 | 50/20 | 20 | 97/100 | 19 | 33 |
| 4 | RES | 3 | 4 | 2 | H | 100/30 | nd | 47/20 | 13 | 100/100 | 10.4 | 34 |
| 5 | RES | 3 | 3 | 4 | H | 100/30 | 0.05 | 65/20 | 9.6 | 97/100 | 15.1 | 75 |
| 6 | RES | 3 | 3 | 2 | H | 73/30 | nd | 50/20 | 20.6 | 100/100 | 4.1 | 19 |
| 7 | RES | 4 | 4 | 2 | H | 100/30 | nd | 68/20 | 12 | 100/100 | 13.6 | 16 |
| 8 | RES | 4 | 3 | 4 | H | 100/30 | 0.52 | 100/20 | 3.7 | 69/100 | 39.3 | 22 |
| 9 | RES | 4 | 3 | 4 | 2-NO$_2$ | 100/30 | nd | 65/20 | 15 | 53/100 | 48.4 | 40 |
| 10 | RES | 4 | 4 | 2 | 40NO$_2$ | 100/30 | nd | 66/20 | 13 | 89/100 | 15.2 | 14 |
| 11 | ClBPIP | 2 | 4 | 2 | H$^d$ | 97/30 | 0.02 | 25/20 | nd | 36/100 | 120 | 10 |
| 12 | ClBPIP | 3 | 3 | 2 | H$^d$ | 100/30 | <0.01 | 85/20 | 7.1 | 69/100 | 16 | 17 |
| 13 | ClBPIP | 3 | 4 | 2 | H$^e$ | 100/30 | 7.6 | 28/20 | nd | 79/100 | 41 | nd |

TABLE I-continued

Biological properties in vitro of derivatives of hydroxyarylsulfanylbenzoic acids (1, n = 0)

| Compound No. | $Z^a$ | Position M | —S— | COOH | X | Inh. of $LTB_4$ biosynth. %/μg | $IC_{50}{}^b$ | Inh. of $LTB_4$ rec. binding %/μM | $IC_{50}{}^c$ | Inh. of $LTD_4$ rec. binding %/μM | $IC_{50}{}^c$ | Antiox. effect %/100 μg |
|---|---|---|---|---|---|---|---|---|---|---|---|---|
| 14 | CIBPIP | 4 | 4 | 2 | $H^f$ | 100/30 | 9.5 | 16/20 | nd | 86/100 | 33 | nd |
| 15 | HOEPIP | 3 | 3 | 2 | H | 88/30 | 12.6 | nd | nd | 22/100 | nd | 0 |
| 16 | QUIN | 1 | 4 | 4 | H | 98/30 | 0.004 | 19/20 | 91.6 | 100/100 | 0.024 | 13 |
| 17 | QUIN | 1 | 3 | 2 | H | 100/30 | 0.08 | 38/20 | 44.2 | 100/100 | 0.63 | 4 |
| 18 | QUIN | 1 | 3 | 4 | H | 100/30 | 0.02 | 24/20 | 92.9 | 100/100 | 1.6 | 16 |
| 19 | QUIN | 1 | 3 | 2 | H | 100/30 | 0.13 | 34/20 | 70.3 | 100/100 | 1.7 | 10 |
| 20 | CIQUIN | 1 | 3 | 2 | H | 99/30 | 0.035 | 31/20 | 31.3 | 100/100 | 0.27 | 1 |
| 21 | CIQUIN | 1 | 4 | 2 | H | 100/30 | 0.08 | 39/20 | 30.1 | 86/100 | 1.7 | 0 |
| 22 | CIQUIN | 1 | 4 | 4 | H | 97/30 | 0.07 | 22/20 | 50 | 84/100 | 3.8 | 13 |
| 23 | $CIQUIN^g$ | 1 | 3 | 2 | H | 96/30 | 0.96 | 33/20 | 13.5 | 99/20 | 0.1 | 9 |
| 24 | $QUIN^g$ | 1 | 4 | 4 | H | 99/30 | 0.18 | 42/20 | 14.7 | 95/20 | 0.31 | 13 |
| Standards | | | | | | | | | | | | |
| Tenidap $Na^+$ | | | | | | 100/30 | 1.04 | 8/20 | nd | 10/100 | 418.3 | nd |
| Zileuton | | | | | | 100/30 | 0.17 | 28/20 | nd | 7/100 | nd | nd |
| Accolate | | | | | | 98/30 | 1.12 | 0/20 | nd | 94/100 | 0.03 | nd |

[a] RES - 4-acetyl-3-hydroxy-2-propylphenoxy, CIBPIP - 4-chlorobenzylpiperazinyl, HOEPIP - 2-hydroxyethylpiperazinyl, QUIN - 2-quinolinyl, CIQUIN - 6-chloroquinolinyl;
[b] in μg · $ml^{-1}$;
[c] in μM · $Lt^{-1}$;
[d] isolated as dimaleate;
[e] isolated as mesylate;
[f] isolated as hydrochloride;
[g] isolated as bis-(hydroxymethyl)methylammonium salt

TABLE II

Biological properties in vitro of derivatives of hydroxyarylsulfanylphenylacetic acid

| Compound No. | $Z^a$ | Position M | —S— | COOH | X | Inh. of $LTB_4$ biosynth. %/μg | $IC_{50}{}^b$ | Inh. of $LTB_4$ rec. binding %/μM | $IC_{50}{}^c$ | Inh. of $LTD_4$ rec. binding %/μM | $IC_{50}{}^c$ | Antiox. effect %/100 μg |
|---|---|---|---|---|---|---|---|---|---|---|---|---|
| 25 | RES | 3 | 4 | 2 | H | 100/30 | nd | 19/20 | nd | 71/100 | 37.5 | 23 |
| 26 | RES | 4 | 4 | 2 | H | 97/30 | nd | 29/20 | 18 | 63/100 | 34.7 | 0 |
| 27 | CIBPIP | 3 | 4 | 2 | H | 89/30 | 9.2 | 12/20 | nd | 22/100 | nd | 20 |
| 28 | CIBPIP | 3 | 3 | 2 | H | 100/30 | 0.6 | 69/20 | 7.9 | 10/20 | nd | 3 |
| 29 | QUIN | 1 | 4 | 2 | H | 44/30 | 28 | 50/20 | 24 | 95/100 | 0.6 | 0 |
| 30 | QUIN | 1 | 4 | 4 | H | 94/30 | 0.004 | 43/20 | 20.5 | 80/20 | 2.3 | 14 |
| 31 | CIQUIN | 1 | 3 | 2 | H | 100/30 | 0.46 | 40/20 | 58.9 | 83/20 | 1.15 | 4 (s) |
| 32 | CIQUIN | 1 | 4 | 2 | H | 62/30 | nd | 38/20 | 30 | 81/100 | 1 | 14 |

[a] RES - 4-acetyl-3-hydroxy-2-propylphenoxy, CIBPIP - 4-chlorobenzylpiperazinyl, QUIN - 2-quinolinyl, CIQUIN - 6-chloroquinolinyl;
[b] in μg · $ml^{-1}$;
[c] in μM · $Lt^{-1}$;

TABLE III

Antiinflammatory activities of derivatives of hydroxyarylsulfanylbenzoic acid and hydroxyarylsulfanylphenylacetic acids

| Compound No. | $CE^a$ % of inh. | Experimental pleuritis, % of $inh.^b$ A | B | C | Ear edema, % of $inh.^c$ D | E |
|---|---|---|---|---|---|---|
| 1 | 31 | $8^n$ | 17 | $9^n$ | 13 | $8^n$ |
| 2 | 30 | $2^n$ | 43 (s) | 46 (s) | 18 | $2^n$ |
| 3 | 32 | $2^n$ | 27 | 28 | 8 | $5^n$ |
| 4 | 35 | $10^n$ | 35 | 30 | $6^n$ | $2^n$ |
| 5 | 14 | 10 | 46 (s) | 61 (s) | $1^n$ | 0 |
| 6 | 22 | 26 | 29 | $6^n$ | 9 | $8^n$ |
| 7 | 41 | 14 | 35 | 26 | 16 | $5^n$ |
| 8 | 24 | $7^n$ | 18 | $11^n$ | $1^n$ | 9 (s) |
| 9 | 19 | 34 | 54 | 30 | 14 | $2^n$ |
| 10 | 22 | 14 | 31 | 19 | 20 | $2^n$ |
| 11 | 33 | nd | nd | nd | 22 | 0 |
| 12 | 27 | nd | nd | nd | 18 | $7^n$ |
| 15 | 9 | $2^n$ | 15 (s) | 11 (sú | 7 | $3^n$ |
| 16 | 25 | 26 | 33 | 11 | 27 | $3^n$ |
| 17 | 19 | $5^n$ | 20 | 15 | 16 | $3^n$ |
| 18 | 10 | 28 | 29 | $1^n$ | 13 | $8^n$ |
| 19 | 13 | 17 | 23 | $6^n$ | 20 | $5^n$ |
| 20 | 25 | 15 | 19 | $4^n$ | 12 | 0 |

TABLE III-continued

Antiinflammatory activities of derivatives of hydroxyarylsulfanylbenzoic acid and hydroxyarylsulfanylphenylacetic acids

| Compound No. | $CE^a$ % of inh. | Experimental pleuritis, % of inh.[b] | | | Ear edema, % of inh.[c] | |
|---|---|---|---|---|---|---|
| | | A | B | C | D | E |
| 21 | 18 | 15 | 12 | 4 (s) | 7 | $3^n$ |
| 22 | 14 | 10 | 25 | 15 | $1^n$ | $9^n$ |
| 23 | 50 | 17 | 31 | 17 | 1 (s) | 8 |
| 24 | 27 | 23 | 32 | 6 | nd | nd |
| 25 | 7 | $4^n$ | 38 (s) | 44 (s) | 20 | 16 |
| 26 | 34 | 20 | $8^n$ | 23 | 17 | 0 |
| 27 | 13 | 8 | 61 (s) | 47 (s) | $7^n$ | 22 |
| 28 | 18 | 10 | 21 | 14 | 16 | 19 |
| 29 | 52 | 3 (s) | 27 (s) | 25 (s) | $2^n$ | 22 |
| 30 | 41 | 27 | 30 | $2^n$ | nd | nd |
| 31 | 13 | 24 (s) | 75 (s) | 39 (s) | 16 | 11 |
| Standards: | | | | | | |
| Tenidap Na+ | 61 | 72 | 73 | $6^n$ | 14 | 76 |
| Zileuton | 46 | 36 | 49 | 20 | $9^n$ | 13 |

[a]inhibition of carrageenan-induced edema after the dose 100 mg kg;
[b]inhibition after the dose of 100 mg/kg: A volume of exudate in pleural cavity; B number of cells; C cellularity in a volume unit;
[c]inhibition after the dose of 200 mg/kg: D edema of ear lobe, E hyperemia of ear lobe;
[n]the level of statistical significance $p > 0.05$;
nd - not determined

TABLE IV

Inhibition of bronchspasm induced by selected mediators (dose: 100 mg/kg; % of inhibiton at 2, 4 and 10 min intervals)

| Compound No. | Mediators | |
|---|---|---|
| | Ovalbumin | $LTD_4$ |
| 5 | nd | nd, 16, nd |
| 8 | nd | nd, 98, nd |
| 12 | 71, 73, 90 | 9, 41, $60^a$ |
| 13 | 46, 35, 51 | 6, 38, $54^b$ |
| 16 | 41, 45, 63 | 69, 70.75 |
| 17 | 23, 36, 50 | 11, 28, 23 |
| 19 | 21, 27.31 | 14, 33, 43 |
| 20 | 66, 72, 85 | 6, 38, 54 |
| 22 | 3, 15, 30 | 14, 33, 43 |
| Standards | | |
| E 5110 | 74, 71, 69 | 45, 55, 58 |
| Zileuton | 23, 28, 50 | 10, 54, 75 |

[a]Inhibition of bronchospasm induced by histamine liberator 48/80: 77, 78, 85%; [b]inhibition of bronchospasm induced by histamine liberator 48/80: 84, 82, 69%

What is claimed is:

1. A compound of Formula (I):

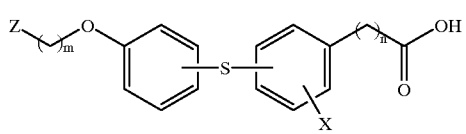

(I)

wherein X is H, halogen or $NO_2$ group, n is 0 or 1, and m is 2 to 4 if Z is either 4-acetyl-3-hydroxy-2-propylphenoxy of Formula (II):

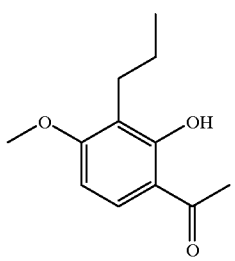

(II)

or piperazinyl residue of Formula (III):

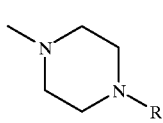

(III)

wherein R is alkyl of 1 to 4 carbon atoms, benzyl, susbtituted benzyl, or hydroxymethyl;

or m is 1, if Z is a quinoline-2-yl residue of Formula (IV):

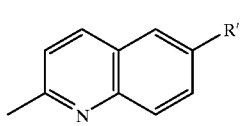

(IV)

wherein R' is H or halogen.

2. The compound according to claim 1, wherein said compound of Formula (I) is selected from the group consisting of 4-(3-(4-(4-acetyl-3-hydroxy-2-propylphenoxy)butoxy)phenylsulfanyl)benzoic acid, 2-(3-(3-(1-(4-chlorobenzyl)piperazin-4-yl)propoxy)phenylsulfanyl)benzoic acid, 2-(4-(3-(1-(4-chlorobenzyl)piperazin-4-yl)propoxy)phenylsulfanyl)benzoic acid, 4-(4-(quinoline-2-ylmethoxy)phenylsulfanyl)benzoic acid, 2-(3-(6-chloroquinoline-2-ylmethoxy)phenylsulfanyl)benzoic acid and 2-(4-(4-(4-acetyl-3-hydroxy-2-propylphenoxy)propoxy)phenylsulfanyl)phenylacetic acid.

3. A process for the preparation of the compound of Formula (I) according to claim 1, comprising:

reacting a compound of Formula (VII):

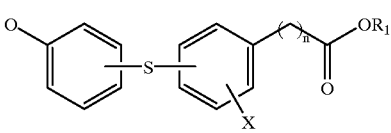

(VII)

wherein X is the same as in Formula (I) and $R_1$ is methyl or ethyl, with a compound of Formula (VIII):

$Z(CH_2)_m Hal$ (VIII)

wherein Z is a group of Formulas II or IV;
m is the same as in Formula (I) and Hal is Cl, Br, or I;
wherein Z in Formula (I) is a group of Formulas (II) or (IV).

4. A pharmaceutical composition, comprising:

the compound of Formula (I) according to claim 1 or a pharmaceutically acceptable salt thereof; and a pharmaceutically acceptable carrier.

5. A method for treating inflammation or asthma, comprising:

administering the pharmaceutical composition according to claim 4 to a subject in need thereof.

6. A process for the preparation of the compound of Formula (I) according to claim 1, comprising:

reacting an ester of ω-haloalkylphenylsulfanylbenzoic or arylacetic acid of Formula (V):

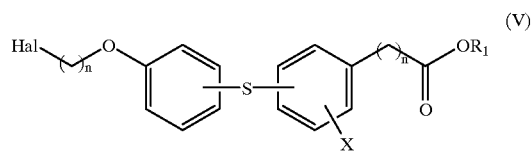

(V)

wherein
Hal is Cl, Br, or I;
R is methyl or ethyl;
m, n and X are the same as in Formula (I);
with a compound of Formula (VI):

Z—H  (VI)

wherein Z is a group of Formulas (II) or (III);
wherein Z in the compound of Formula (I) is a group of Formulas (II) or (III).

* * * * *

UNITED STATES PATENT AND TRADEMARK OFFICE
CERTIFICATE OF CORRECTION

PATENT NO. : 6,303,612 B1
DATED : October 16, 2001
INVENTOR(S) : Kuchař et al.

It is certified that error appears in the above-identified patent and that said Letters Patent is hereby corrected as shown below:

<u>Title page,</u>
Item 54, and at top of Column 1, the title should read:
-- [54] DERIVATIVES OF HYDROXYPHENYLSULFANYLBENZOIC AND HYDROXYPHENYLSULFANYLARYLACETIC ACIDS --
Item [75], the Inventors information should read:
-- [75] Inventors: Miroslav Kuchař; Vojtěch Kmoníček; Vladimíra Panajotová; Bohumila Brůnová; Antonín Jandera; Hana Jiříčková; Věra Bucharová, all of Praha CZ) --
Item [30], the Foreign Application Priority information should read:
-- [30]         Foreign Application Priority Data
Jun. 19, 1998         (CZ) ........................................ PV 1941-98 --

Signed and Sealed this

Twenty-eighth Day of May, 2002

Attest:

JAMES E. ROGAN
Attesting Officer     Director of the United States Patent and Trademark Office